United States Patent [19]
Zhou et al.

[11] Patent Number: 6,110,738
[45] Date of Patent: Aug. 29, 2000

[54] HUMAN FAST-1 GENE

[75] Inventors: Shibin Zhou, Cockeysville; Leigh Zawel, Bowie; Bert Vogelstein, Baltimore; Kenneth W. Kinzler, BelAir, all of Md.

[73] Assignee: The Johns Hopkins University, Baltimore, Md.

[21] Appl. No.: 09/113,309

[22] Filed: Jul. 10, 1998

[51] Int. Cl.$^7$ ............... C12N 5/10; C12N 1/00; C12N 15/12; C12N 15/63

[52] U.S. Cl. ............. 435/325; 435/243; 435/320.1; 435/410; 536/23.5

[58] Field of Search .................. 536/23.1, 23.5, 536/24.31, 24.33; 435/320.1, 325, 410, 243

[56] References Cited

FOREIGN PATENT DOCUMENTS

WO88/09386  12/1988  WIPO.
98-53830    12/1998  WIPO.

OTHER PUBLICATIONS

EMBL Database, Heidelberg, FRG Accession number EMEST20:AA218611 Feb. 12, 1997, Hillier, L. Et al. "Zq97H05.rl s NT2 neuronal precursor 937230 Homo sapiens cDNA clone 649977 5'".

Zhou, S. Et al. "Targeted deletion of Smad4 shows it is required for transforming growth factor beta and activin signaling in colorectal cancer cells" Proceedings of the National Academy of Sciences of USA, vol. 95, No. 5, Mar. 3, 1998.

EMBL Database, Heidelberg, FRG Accession number Emvrt;U70980 Nov. 1, 1996, Rubock, MJ. et al. "Xenopus laevis forkhead activin signal transducer 1 mRNA complete cds".

Chen X et al. "A transcriptional partner for MAD proteins in TGF–beta signatlling" Nature, vol. 383, No. 6602, Oct. 24, 1996, pp. 691–696.

Liu, F. et al. "Dual role of the Smad4/DPC4 tumor suppressor in TGFbeta–inducible transcriptional complexes" Genes & Development, vol. 11, No. 23, Dec. 1, 1997 pp. 3157–3167.

Zhou S. et al. "Ahcaracterization of Human Fast–1, a TGFbeta and Activin Signal Transducer" Molecular Cell, vol. 2, No. 1, Jul. 23, 1998, pp. 121–127.

Chen, Genbank Accession U70980—97032727, Jun. 26, 1997.

Clevidence, Genbank Accession L13205—Medline 93248207, Jun. 23, 1993.

Haecker, Genbank Accession M96441—Medline 92409595, May 5, 1993.

Grossniklaus, Genbank Accession X66095 S37037—Medline 92275347, Nov. 22, 1993.

Grossniklaus, Genbank Accession X66096—Medline 92275347, Nov. 26, 1992.

Celniker, Genbank Accession AC005732, AC004781, AC004329, AC004427, AC003768, AC003769, AC003298, AC003770, AC003299, AC003771, AC003300, AC003772, AC003301, AC003773, AC003302, AC003303, AC003304, AC003305, AC003774, AC003775, A003776, AC004714—Locus AC005732, Oct. 2, 1998.

Ye, Genbank Accession U74613—Medline 97184488, Mar. 6, 1997.

Ye, Genbank Accession U74612—Medline 97184488, Mar. 6, 1997.

Yao, Genbank Accession U83113—Medline 97390411, Oct. 13, 1998.

*Primary Examiner*—Terry McKelvey
*Attorney, Agent, or Firm*—Banner & Witcoff, Ltd.

[57] ABSTRACT hFAST-1 is a human forkhead activin signal transducer gene. The hFAST-1 protein has the ability to bind to human Smad2 and activate an activin response element (ARE). The hFAST-1-dependent activation of ARE is dependent on endogenous Smad4 and stimulation of the TGF-β receptor. The hFAST-1 protein binds to a novel DNA motif, TGT(G/T)(T/G)ATT, which is present within the ARE. This motif is important for the activation of genes responsive to ligands of the TGF-β family. The invention includes tools for investigating the TGF-β signaling pathway and screening for compounds which modulate the action of TGF-β.

12 Claims, 4 Drawing Sheets

FIG. 1

| | | |
|---|---|---:|
| hFAST-1 | ngpdsgsrlgppeaespsqpp--------------------------------- | 21 |
| xFAST-1 | mrdpsslysgfpagsqyesveppslallssidqeqlpvatgqsynhsvqpw | 51 |
| hFAST-1 | ------------------------------------------------- | 21 |
| xFAST-1 | pqpwpplslyreggtwspdrgsmyglspgthegscththegpkdsmagdht | 102 |
| hFAST-1 | ---KRRKKRYLRHDKPPYTYLAMIALVIQAAPSRRLKLAQIIRQVQAVFPF | 69 |
| xFAST-1 | rsrKSKKKNYHRYYKPPYSYLAMIALVIQNSPEKRLKLSQILKEVSTLFPF | 153 |
| hFAST-1 | FREDYEGWKDSIRHNLSSNRCFRKVPKDPAKPQAKGNFWAMDVSLITPAEAL | 120 |
| xFAST-1 | FNGDYMGWKDSIRHNLSSSDCFKKILKDPGKPQAKGNFWTMDVSRIPLDAM | 204 |
| hFAST-1 | RLQNTALCRrwqngGARGAFAKDLGPYVLHGRPYrppspppppsegfsiks | 171 |
| xFAST-1 | KLQNTALTR----GGSDYFVQDLAPYILHNYKYehnagayghqmppshar | 250 |
| hFAST-1 | lllggsgegapwpglapqsspvpagtgnsgeeavptpplpsserplwplcpl | 222 |
| xFAST-1 | slslaedsqqtntggklntsfmidsllhdlqevdlpdasrnlenqrispav | 301 |
| hFAST-1 | pgptrvegetvqggaigpstlspeprawplhllqgtavpggrssgghrasl | 273 |
| xFAST-1 | amnnmwssapllythskptrnarspglstihstysssssssistispvgfqk | 352 |
| hFAST-1 | wgq----------------------------------------------- | 276 |
| xFAST-1 | eqeksgrqtqrvghpikrsredddcsttssdpdtgnyspieppkkmpllsl | 403 |
| hFAST-1 | -LPTSMLPIYTPNVVMPlapppstscpqcpstspaywgvapetrgppgllc- | 325 |
| xFAST-1 | dLPTSMTKSVAPNVVAPpsvlpffhfprftyynygpspymtppywgfphpt | 454 |
| hFAST-1 | ------------DLDALFQGVPPNKSIYDMVSHPRDLAApgpwllsw | 362 |
| xFAST-1 | nsggdsprgpqsplDLDNMLRAMPPNKSVFDMLTSHPGDLVHPsflsqclg | 505 |
| hFAST-1 | csl---------- | 365 |
| xFAST-1 | ssgspypsrqglm | 518 |

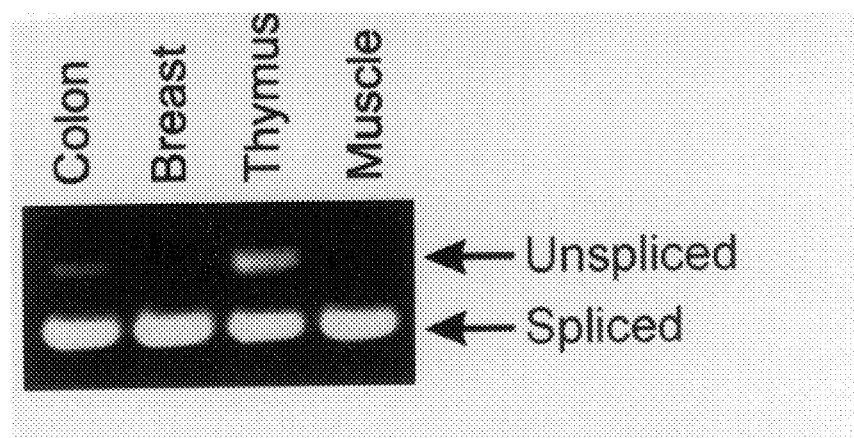
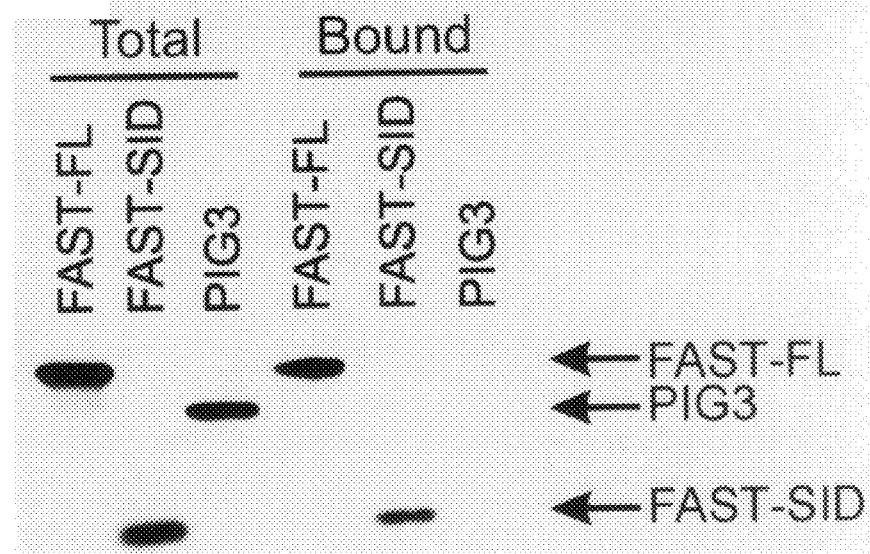

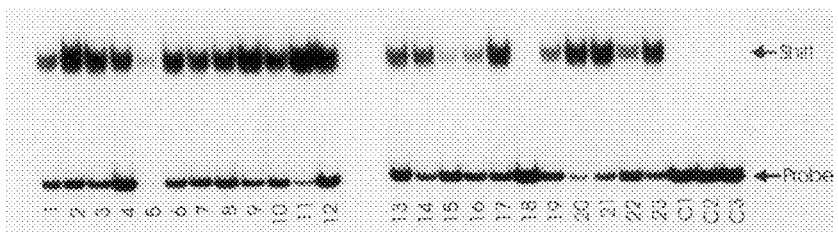
FIG. 4A
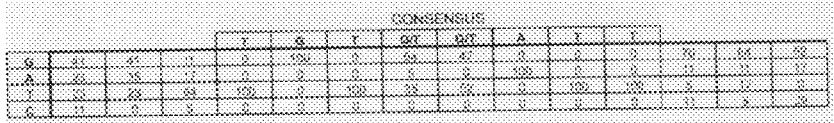
FIG. 4B
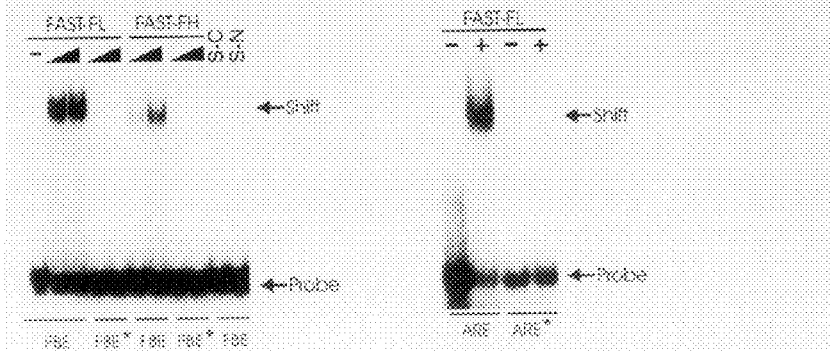
FIG. 4C
FIG. 4D

SEQUENCE LISTING

```
<160> NUMBER OF SEQ ID NOS: 19

<210> SEQ ID NO 1
<211> LENGTH: 1793
<212> TYPE: DNA
<213> ORGANISM: Homo sapiens

<400> SEQUENCE: 1
gttgagtcaa tgtgtccccc tcttgttcct agggtgcggg cttcatggcc ttctcctcca      60
ggaagctcca cctgatcatg tcctgggtgg atatccagcc cccatagttc agggcctact     120
agcagctgct agatcttgaa ctccaggagc gccccacgcc ttgggagctt ggcatgggct     180
aaatactccc ccatttgtta aatgggtcc tgaaacctga ccagggaaga cgggataaag      240
tagccatggg tcatcgcagc ccctttgaag ccgggcctgg ccacccaaag gcaactcagg     300
ggtggagact gaggcctcag gagaagcccc cactagaatg ctctctgccc ctcccttcca     360
gattaaccaa aacctgctaa ttgtggaagc cctcggcatg ctcccctccc ccacagcctc     420
ttcctccctt ccctcccctc cccttccat ccgaatgata aaggcccag cccgcctgcc      480 ccagcccggc ctcaggtccc ggcctgcct tctacactgc cccaccgccc tgcaccctcc     540
acccggccag gcccctgccc acgctgtcta ccgtcccgca tggggccctg cagcggctcc     600
cgcctggggc ccccagaggc agagtcgccc tcccagcccc ctaagaggag gaagaagagg     660
```

```
tacctgcgac atgacaagcc ccctacacc tacttggcca tgatcgcctt ggtgattcag    720
gccgctccct cccgcagact gaagctggcc cagatcatcc gtcaggtcca ggccgtgttc    780
cccttcttca gggaagacta cgagggctgg aaagactcca ttcgccacaa cctttcctcc    840
aaccgatgct tccgcaaggt gcccaaggac cctgcaaagc ccaggccaa gggcaacttc    900 tgggcggtcg acgtgagcct gatcccagct gaggcgctcc ggctgcagaa caccgccctg    960
tgccggcgct ggcagaacgg aggtgcgcgt ggagccttcg ccaaggacct gggcccctac   1020
gtgctgcacg gccggccata ccggccgccc agtcccccgc caccccag tgagggcttc   1080 agcatcaagt ccctgctagg agggtccggg gaggggcac cctggccggg gctagctcca   1140
cagagcagcc cagttcctgc aggcacaggg aacagtgggg aggaggcggt gcccacccca   1200
ccccttccct cttctgagag gcctctgtgg ccctctgcc ccttcctgg ccccacgaga   1260 gtggagggg agactgtgca gggggagcc atcgggccct caaccctctc cccagagcct   1320
agggcctggc ctctccactt actgcagggc accgcagttc ctggggacg tccagcggg   1380 ggacacaggg cctccctctg ggggcagctg cccacctcct acttgcctat ctacactccc   1440
aatgtggtaa tgcccttggc accaccaccc acctcctgtc cccagtgtcc gtcaaccagc   1500
cctgcctact gggggtggc ccctgaaacc cgagggcccc cagggctgct ctgcgatcta   1560
gacgccctct tccaagggt gccacccaac aaaagcatct acgacgtttg ggtcagccac   1620
cctcgggacc tggcggcccc tggcccaggc tggctgctct cctggtgcag cctgtgaggc   1680
tcttaagaca ggggccgctc ctccctcccg ctcccacccc caccttgttg acagggagca   1740
agggaggcgg ctgtctgcga cacagcagct cgaaaaccag gcagagcttg ttg           1793

<210> SEQ ID NO 2
<211> LENGTH: 365
<212> TYPE: PRT
<213> ORGANISM: Homo sapiens

<400> SEQUENCE: 2

Met Gly Pro Cys Ser Gly Ser Arg Leu Gly Pro Glu Ala Glu Ser
 1               5                  10                  15

Pro Ser Gln Pro Pro Lys Arg Arg Lys Lys Arg Tyr Leu Arg His Asp
                 20                  25                  30

Lys Pro Pro Tyr Thr Tyr Leu Ala Met Ile Ala Leu Val Ile Gln Ala
             35                  40                  45

Ala Pro Ser Arg Arg Leu Lys Leu Ala Gln Ile Ile Arg Gln Val Gln
         50                  55                  60

Ala Val Phe Pro Phe Phe Arg Glu Asp Tyr Glu Gly Trp Lys Asp Ser
 65                  70                  75                  80

Ile Arg His Asn Leu Ser Ser Asn Arg Cys Phe Arg Lys Val Pro Lys
                 85                  90                  95

Asp Pro Ala Lys Pro Gln Ala Lys Gly Asn Phe Trp Ala Val Asp Val
            100                 105                 110

Ser Leu Ile Pro Ala Glu Ala Leu Arg Leu Gln Asn Thr Ala Leu Cys
        115                 120                 125

Arg Arg Trp Gln Asn Gly Gly Ala Arg Gly Ala Phe Ala Lys Asp Leu
    130                 135                 140

Gly Pro Tyr Val Leu His Gly Arg Pro Tyr Arg Pro Ser Pro Pro
145                 150                 155                 160

Pro Pro Pro Ser Glu Gly Phe Ser Ile Lys Ser Leu Leu Gly Gly Ser
                165                 170                 175
```

```
Gly Glu Gly Ala Pro Trp Pro Gly Leu Ala Pro Gln Ser Ser Pro Val
            180                 185                 190

Pro Ala Gly Thr Gly Asn Ser Gly Glu Glu Ala Val Pro Thr Pro Pro
            195                 200                 205

Leu Pro Ser Ser Glu Arg Pro Leu Trp Pro Leu Cys Pro Leu Pro Gly
            210                 215                 220

Pro Thr Arg Val Glu Gly Glu Thr Val Gln Gly Gly Ala Ile Gly Pro
225                 230                 235                 240

Ser Thr Leu Ser Pro Glu Pro Arg Ala Trp Pro Leu His Leu Leu Gln
            245                 250                 255

Gly Thr Ala Val Pro Gly Gly Arg Ser Ser Gly Gly His Arg Ala Ser
            260                 265                 270

Leu Trp Gly Gln Leu Pro Thr Ser Tyr Leu Pro Ile Tyr Thr Pro Asn
            275                 280                 285

Val Val Met Pro Leu Ala Pro Pro Thr Ser Cys Pro Gln Cys Pro
            290                 295                 300

Ser Thr Ser Pro Ala Tyr Trp Gly Val Ala Pro Glu Thr Arg Gly Pro
305                 310                 315                 320

Pro Gly Leu Leu Cys Asp Leu Asp Ala Leu Phe Gln Gly Val Pro Pro
            325                 330                 335

Asn Lys Ser Ile Tyr Asp Val Trp Val Ser His Pro Arg Asp Leu Ala
            340                 345                 350

Ala Pro Gly Pro Gly Trp Leu Leu Ser Trp Cys Ser Leu
            355                 360                 365

<210> SEQ ID NO 3
<211> LENGTH: 477
<212> TYPE: PRT
<213> ORGANISM: Homo sapiens

<400> SEQUENCE: 3

Val Ala Met Ile Asn Ala Cys Ile Asp Ser Met Ser Ser Ile Leu Pro
1               5                   10                  15

Phe Thr Pro Pro Val Val Lys Arg Leu Leu Gly Trp Lys Lys Ser Ala
            20                  25                  30

Gly Gly Ser Gly Gly Ala Gly Gly Gly Glu Gln Asn Gly Gln Glu Glu
            35                  40                  45

Lys Trp Cys Glu Lys Ala Val Lys Ser Leu Val Lys Lys Leu Lys Lys
        50                  55                  60

Thr Gly Arg Leu Asp Glu Leu Glu Lys Ala Ile Thr Thr Gln Asn Cys
65              70                  75                  80

Asn Thr Lys Cys Val Thr Ile Pro Ser Thr Cys Ser Glu Ile Trp Gly
                85                  90                  95

Leu Ser Thr Pro Asn Thr Ile Asp Gln Trp Asp Thr Thr Gly Leu Tyr
            100                 105                 110

Ser Phe Ser Glu Gln Thr Arg Ser Leu Asp Gly Arg Leu Gln Val Ser
            115                 120                 125

His Arg Lys Gly Leu Pro His Val Ile Tyr Cys Arg Leu Trp Arg Trp
        130                 135                 140

Pro Asp Leu His Ser His His Glu Leu Lys Ala Ile Glu Asn Cys Glu
145                 150                 155                 160

Tyr Ala Phe Asn Leu Lys Lys Asp Glu Val Cys Val Asn Pro Tyr His
                165                 170                 175

Tyr Gln Arg Val Glu Thr Pro Val Leu Pro Pro Val Leu Val Pro Arg
```

```
                180                 185                 190
His Thr Glu Ile Leu Thr Glu Leu Pro Pro Leu Asp Asp Tyr Thr His
            195                 200                 205

Ser Ile Pro Glu Asn Thr Asn Phe Pro Ala Gly Ile Glu Pro Gln Ser
210                 215                 220

Asn Tyr Ile Pro Glu Thr Pro Pro Gly Tyr Ile Ser Glu Asp Gly
225                 230                 235                 240

Glu Thr Ser Asp Gln Gln Leu Asn Gln Ser Met Asp Thr Gly Ser Pro
            245                 250                 255

Ala Glu Leu Ser Pro Thr Thr Leu Ser Pro Val Asn His Ser Leu Asp
            260                 265                 270

Leu Gln Pro Val Thr Tyr Ser Glu Pro Ala Phe Trp Cys Ser Ile Ala
            275                 280                 285

Tyr Tyr Glu Leu Asn Gln Arg Val Gly Glu Thr Phe His Ala Ser Gln
            290                 295                 300

Pro Ser Leu Thr Val Asp Gly Phe Thr Asp Pro Ser Asn Ser Glu Arg
305                 310                 315                 320

Phe Cys Leu Gly Leu Leu Ser Asn Val Asn Arg Asn Ala Thr Val Glu
            325                 330                 335

Met Thr Arg Arg His Ile Gly Arg Gly Val Arg Leu Tyr Tyr Ile Gly
            340                 345                 350

Gly Glu Val Phe Ala Glu Cys Leu Ser Asp Ser Ala Ile Phe Val Gln
            355                 360                 365

Ser Pro Asn Cys Asn Gln Arg Tyr Gly Trp His Pro Ala Thr Val Cys
            370                 375                 380

Lys Ile Pro Pro Gly Cys Asn Leu Lys Ile Phe Asn Asn Gln Glu Phe
385                 390                 395                 400

Ala Ala Leu Leu Ala Gln Ser Val Asn Gln Gly Phe Glu Ala Val Tyr
            405                 410                 415

Gln Leu Thr Arg Met Cys Thr Ile Arg Met Ser Phe Val Lys Gly Trp
            420                 425                 430

Gly Ala Glu Tyr Arg Arg Gln Thr Val Thr Ser Thr Pro Cys Trp Ile
            435                 440                 445

Glu Leu His Leu Asn Gly Pro Leu Gln Trp Leu Asp Lys Val Leu Thr
            450                 455                 460

Gln Met Gly Ser Pro Ser Val Arg Cys Ser Ser Met Ser
465                 470                 475

<210> SEQ ID NO 4
<211> LENGTH: 8
<212> TYPE: DNA
<213> ORGANISM: Homo sapiens

<400> SEQUENCE: 4 tgtkkatt                                                               8

<210> SEQ ID NO 5
<211> LENGTH: 18
<212> TYPE: DNA
<213> ORGANISM: Homo sapiens

<400> SEQUENCE: 5
ctggaaagac tccattcg                                                   18

<210> SEQ ID NO 6
<211> LENGTH: 19
```

```
<212> TYPE: DNA
<213> ORGANISM: Homo sapiens

<400> SEQUENCE: 6
cacagaggcc tctcagaag                                             19

<210> SEQ ID NO 7
<211> LENGTH: 18
<212> TYPE: DNA
<213> ORGANISM: Homo sapiens

<400> SEQUENCE: 7
cccccttcca tccgaatg                                              18

<210> SEQ ID NO 8
<211> LENGTH: 19
<212> TYPE: DNA
<213> ORGANISM: Homo sapiens

<400> SEQUENCE: 8
gagctgctgt gtcgcagac                                             19

<210> SEQ ID NO 9
<211> LENGTH: 79
<212> TYPE: DNA
<213> ORGANISM: Artificial Sequence
<220> FEATURE:
<223> OTHER INFORMATION: flag primer

<400> SEQUENCE: 9
ggatcctaat acgactcact atagggagac caccatggac tacaaggacg acgatgacaa    60
ggggccctgc agcggctcc                                             79

<210> SEQ ID NO 10
<211> LENGTH: 81
<212> TYPE: DNA
<213> ORGANISM: Artificial Sequence
<220> FEATURE:
<223> OTHER INFORMATION: flag primer

<400> SEQUENCE: 10
ggatcctaat acgactcact atagggagac caccatggac tacaaggacg acgatgacaa    60
gccccttcct ggccccacga g                                          81

<210> SEQ ID NO 11
<211> LENGTH: 31
<212> TYPE: DNA
<213> ORGANISM: Homo sapiens

<400> SEQUENCE: 11
tatgcggccg ccaccatggg gccctgcagc g                               31

<210> SEQ ID NO 12
<211> LENGTH: 30
<212> TYPE: DNA
<213> ORGANISM: Homo sapiens

<400> SEQUENCE: 12
tatgcggccg cgagctgctg tgtcgcagac                                 30

<210> SEQ ID NO 13
<211> LENGTH: 7
<212> TYPE: DNA
```

<213> ORGANISM: Homo sapiens

<400> SEQUENCE: 13 rymaaya                                                                    7

<210> SEQ ID NO 14
<211> LENGTH: 22
<212> TYPE: DNA
<213> ORGANISM: Homo sapiens

<400> SEQUENCE: 14
tagtaaacac tctatcaatt gg                                                  22

<210> SEQ ID NO 15
<211> LENGTH: 20
<212> TYPE: DNA
<213> ORGANISM: Homo sapiens

<400> SEQUENCE: 15
gtccagtatc gtttacagcc                                                     20

<210> SEQ ID NO 16
<211> LENGTH: 21
<212> TYPE: DNA
<213> ORGANISM: Homo sapiens

<400> SEQUENCE: 16
cggattgtgt attggctgta c                                                   21

<210> SEQ ID NO 17
<211> LENGTH: 21
<212> TYPE: DNA
<213> ORGANISM: Homo sapiens

<400> SEQUENCE: 17
cggattctgt atcggctgta c                                                   21

<210> SEQ ID NO 18
<211> LENGTH: 55
<212> TYPE: DNA
<213> ORGANISM: Homo sapiens

<400> SEQUENCE: 18
tatctgctgc cctaaaatgt gtattccatg gaaatgtctg cccttctctc cgtac              55

<210> SEQ ID NO 19
<211> LENGTH: 518
<212> TYPE: PRT
<213> ORGANISM: Xenopus laevis

<400> SEQUENCE: 19

Met Arg Asp Pro Ser Ser Leu Tyr Ser Gly Phe Pro Ala Gly Ser Gln
1               5                   10                  15

Tyr Glu Ser Val Glu Pro Pro Ser Leu Ala Leu Leu Ser Ser Ile Asp
            20                  25                  30

Gln Glu Gln Leu Pro Val Ala Thr Gly Gln Ser Tyr Asn His Ser Val
        35                  40                  45

Gln Pro Trp Pro Gln Pro Trp Pro Leu Ser Leu Tyr Arg Glu Gly Gly
    50                  55                  60

Gly Thr Trp Ser Pro Asp Arg Gly Ser Met Tyr Gly Leu Ser Pro Gly
65                  70                  75                  80

-continued

```
Thr His Glu Gly Ser Cys Thr His Thr His Glu Gly Pro Lys Asp Ser
            85                  90                  95

Met Ala Gly Asp His Thr Arg Ser Arg Lys Ser Lys Lys Lys Asn Tyr
            100                 105                 110

His Arg Tyr Tyr Lys Pro Pro Tyr Ser Tyr Leu Ala Met Ile Ala Leu
            115                 120                 125

Val Ile Gln Asn Ser Pro Glu Lys Arg Leu Lys Leu Ser Gln Ile Leu
            130                 135                 140

Lys Glu Val Ser Thr Leu Phe Pro Phe Phe Asn Gly Asp Tyr Met Gly
145                 150                 155                 160

Trp Lys Asp Ser Ile Arg His Asn Leu Ser Ser Asp Cys Phe Lys
            165                 170                 175

Lys Ile Leu Lys Asp Pro Gly Lys Pro Gln Ala Lys Gly Asn Phe Trp
            180                 185                 190

Thr Val Asp Val Ser Arg Ile Pro Leu Asp Ala Met Lys Leu Gln Asn
            195                 200                 205

Thr Ala Leu Thr Arg Gly Gly Ser Asp Tyr Phe Val Gln Asp Leu Ala
            210                 215                 220

Pro Tyr Ile Leu His Asn Tyr Lys Tyr Glu His Asn Ala Gly Ala Tyr
225                 230                 235                 240

Gly His Gln Met Pro Pro Ser His Ala Arg Ser Leu Ser Leu Ala Glu
            245                 250                 255

Asp Ser Gln Gln Thr Asn Thr Gly Gly Lys Leu Asn Thr Ser Phe Met
            260                 265                 270

Ile Asp Ser Leu Leu His Asp Leu Gln Glu Val Asp Leu Pro Asp Ala
            275                 280                 285

Ser Arg Asn Leu Glu Asn Gln Arg Ile Ser Pro Ala Val Ala Met Asn
290                 295                 300

Asn Met Trp Ser Ser Ala Pro Leu Leu Tyr Thr His Ser Lys Pro Thr
305                 310                 315                 320

Arg Asn Ala Arg Ser Pro Gly Leu Ser Thr Ile His Ser Thr Tyr Ser
            325                 330                 335

Ser Ser Ser Ser Ser Ile Ser Thr Ile Ser Pro Val Gly Phe Gln Lys
            340                 345                 350

Glu Gln Glu Lys Ser Gly Arg Gln Thr Gln Arg Val Gly His Pro Ile
            355                 360                 365

Lys Arg Ser Arg Glu Asp Asp Cys Ser Thr Thr Ser Ser Asp Pro
370                 375                 380

Asp Thr Gly Asn Tyr Ser Pro Ile Glu Pro Lys Lys Met Pro Leu
385                 390                 395                 400

Leu Ser Leu Asp Leu Pro Thr Ser Tyr Thr Lys Ser Val Ala Pro Asn
            405                 410                 415

Val Val Ala Pro Pro Ser Val Leu Pro Phe Phe His Phe Pro Arg Phe
            420                 425                 430

Thr Tyr Tyr Asn Tyr Gly Pro Ser Pro Tyr Met Thr Pro Pro Tyr Trp
            435                 440                 445

Gly Phe Pro His Pro Thr Asn Ser Gly Gly Asp Ser Pro Arg Gly Pro
            450                 455                 460

Gln Ser Pro Leu Asp Leu Asp Asn Met Leu Arg Ala Met Pro Pro Asn
465                 470                 475                 480

Lys Ser Val Phe Asp Val Leu Thr Ser His Pro Gly Asp Leu Val His
            485                 490                 495

Pro Ser Phe Leu Ser Gln Cys Leu Gly Ser Ser Gly Ser Pro Tyr Pro
```

-continued

```
            500                 505                 510
Ser Arg Gln Gly Leu Met
            515
```

HUMAN FAST-1 GENE

The U.S. Government has a paid-up license in this invention and the right in limited circumstances to require the patent owner to license others on reasonable terms as provided for by the terms of USPHS grant CA43460 awarded by the National Institutes of Health.

TECHNICAL FIELD OF THE INVENTION

The invention is related to the area of developmental and cancer genetics. In particular it is related to the field of transcriptional regulation.

BACKGROUND OF THE INVENTION

Substantial progress in understanding the responses to tumor-derived growth factorβ (TGF-β) and related ligands has been made in the last five years (Derynck and Fang, 1997; Hoodless and Wrana, 1998; Kretzschmar and Massague, 1998). The receptors for these ligands have been cloned and shown to be serine/threonine kinases which are activated by binding to ligand. The major substrates for these kinases, besides the receptors themselves, appear to be Smad proteins. The founding member of the Smad family is the product of the Drosophila gene Mad, identified by its requirement in signaling by the TGF-β family member Dpp (Sekelsky et al., 1995). Nine homologs of Mad have since been identified in vertebrate cells and shown to transduce or inhibit signals from specific TGF-β like ligands (Heldin et al., 1997; Derynck and Fang, 1997; Hoodless and Wrana, 1998; Kretzschmar and Massague, 1998).

The phosphorylation of Smad1, Smad2, and Smad3 stimulates their interaction with Smad4 and the transport of the resulting heteromeric complex to the nucleus (Kretzschmar et al., 1997; Lagna et al., 1996; Liu, 1997; Macias-Silva et al., 1996; Nakao et al., 1997; Nakao et al., 1997; Souchelnytskyi et al., 1997). Once in the nucleus, the Smad complex transcriptionally activates specific target genes through activation domains present at the carboxyl termini of these proteins (Liu et al., 1996). Two ways in which Smad activation could lead to transcriptional activation have been identified. First, it has been shown that human Smad3 and Smad4, but not Smad2, can bind to specific DNA sequences and activate transcription of adjacent reporters (Zawel et al., 1998). A similar sequence-specific activity is present in Drosophila Mad (Kim et al., 1997). Second, Smad2 has been shown to bind to the Xenopus forkhead activin signal transducer protein FAST-1 (xFAST-1) and to participate in a complex exhibiting sequence specific binding activity attributable to the xFAST-1 component (Chen et al., 1996; Chen et al., 1997; Liu, 1997). Although Smad4 does not directly bind to xFAST-1, Smad4 is recruited to the xFAST-1/Smad2 complex by Smad2 (Chen et al., 1997; Liu, 1997).

TGF-β-like responses are remarkably widespread in eukaryotes, and are important not only in development but also in cancer (Fynan and Reiss, 1993; Hartsough and Mulder, 1997). Further progress in understanding the varied developmental and oncogenic ramifications of these pathways in mammalian cells depends on knowledge of the relevant mammalian genes. Thus, there is a need in the art for the identification, isolation, purification, and analysis of mammalian and human genes which mediate physiological and pathological responses to TGF-β and related ligands.

SUMMARY OF THE INVENTION

It is an object of the invention to provide reagents and methods for altering TGF-β activity. These and other objects of the invention are provided by one or more of the embodiments described below.

One embodiment of the invention provides an isolated and purified hFAST-1 protein comprising the amino acid sequence shown in SEQ ID NO:2 and naturally occurring biologically active variants thereof.

Another embodiment of the invention provides a fusion protein which comprises a first protein segment and a second protein segment fused to each other by means of a peptide bond. The first protein segment consists of at least thirteen contiguous amino acids selected from the amino acid sequence shown in SEQ ID NO:2.

Still another embodiment of the invention provides an isolated and purified polypeptide which consists of at least thirteen contiguous amino acids of hFAST-1 as shown in SEQ ID NO:2.

Even another embodiment of the invention provides a preparation of antibodies which specifically bind to an hFAST-1 protein as shown in SEQ ID NO:2.

Yet another embodiment of the invention provides a subgenomic polynucleotide which encodes an hFAST-1 protein as shown in SEQ ID NO:2.

Still another embodiment of the invention provides a vector comprising a subgenomic polynucleotide which encodes an hFAST-1 protein as shown in SEQ ID NO:2.

Another embodiment of the invention provides a vector comprising a subgenomic polynucleotide which encodes an hFAST-1 protein as shown in SEQ ID NO:2 and which is intron-free.

Yet another embodiment of the invention provides a vector comprising a subgenomic polynucleotide which comprises the sequence shown in SEQ ID NO:1.

Even another embodiment of the invention provides a recombinant host cell which comprises a polynucleotide. The polynucleotide encodes an hFAST-1 protein as shown in SEQ ID NO:2.

Still another embodiment of the invention provides a recombinant host cell which comprises a polynucleotide. The polynucleotide encodes an hFAST-1 protein as shown in SEQ ID NO:2 and which is intron-free.

Yet another embodiment of the invention provides a recombinant host cell which comprises a polynucleotide. The polynucleotide comprises the sequence shown in SEQ ID NO:1.

A further embodiment of the invention provides a recombinant DNA construct for expressing hFAST-1 antisense nucleic acids. The recombinant DNA construct comprises a promoter and a coding sequence for hFAST-1. The coding sequence consists of at least 12 contiguous base pairs selected from SEQ ID NO:1. The coding sequence is in an inverted orientation with respect to the promoter. Upon transcription from the promoter an RNA is produced which is complementary to native mRNA encoding hFAST-1.

Another embodiment of the invention provides a method of screening test compounds for those which inhibit the action of TGF-β. A test compound is contacted with a first protein and a second protein. The first protein is all or a portion of a Smad2 protein or a naturally occurring biologically active variant thereof The portion of the Smad2 protein is capable of binding to hFAST-1. The second protein is all or a portion of hFAST-1 or a naturally occurring biologically active variant thereof. The portion of hFAST-1 is capable of binding to the portion of the Smad2 protein. An amount selected from the group consisting of (a) the first protein bound to the second protein, (b) the second protein bound to the first protein, (c) the first protein which is not bound to the second protein, and (d) the second protein which is not bound to the first protein is determined. A test compound which decreases the amount of (a) or (b) or increases the amount of (c) or (d) is a candidate compound for inhibiting the action of TGF-β.

Even another embodiment of the invention provides a method of screening test compounds for the ability to decrease or augment TGF-β activity. A cell is contacted with a test compound. The cell comprises a first fusion protein, a second fusion protein, a reporter gene, and hSmad4 protein. The first fusion protein comprises (1) a DNA binding domain or a transcriptional activating domain and (2) all or a portion of an hFAST-1 protein. The portion of hFAST-1 consists of a contiguous sequence of amino acids selected from the amino acid sequence shown in SEQ ID NO:2. The portion of hFAST-1 is capable of binding to Smad2 protein. The second fusion protein comprises (1) a DNA binding domain or a transcriptional activating domain and (2) all or a portion of Smad2 protein, or a naturally occurring biologically active variant thereof. The portion of Smad2 is capable of binding to hFAST-1 protein. When the first fusion protein comprises a DNA binding domain, the second fusion protein comprises a transcriptional activating domain. When the first fusion protein comprises a transcriptional activating domain, the second fusion protein comprises a DNA binding domain. The interaction of the portion of the hFAST-1 protein with the portion of Smad2 protein reconstitutes a sequence-specific transcriptional activating factor. The reporter gene comprises a DNA sequence to which the DNA binding domain of the first or second fusion protein specifically binds. The expression of the reporter gene is measured. A test compound which increases the expression of the reporter gene is a potential drug for increasing TGF-β activity. A test compound which decreases the expression of the reporter gene is a potential drug for decreasing TGF-β activity.

Still another embodiment of the invention provides a method of screening for drugs with the ability to decrease or augment TGF-β activity. A cell is contacted with a test compound and with TGF-β. The cell comprises all or a portion of Smad2 protein or a naturally occurring biologically active variant thereof and all or a portion of hFAST-1 or a naturally occurring biologically active variant thereof The portion of Smad2 protein is capable of binding to hFAST-1. The portion of hFAST-1 is capable of binding to Smad2 protein. The cell also comprises a vector and hSmad4 protein. The vector comprises a reporter gene under the control of an activin response element. The activin response element comprises a DNA motif TGT(G/T)(T/G)ATT as shown in SEQ ID NO:4. Transcription of the reporter gene is measured. A test compound which increases the amount of reporter gene transcription is a potential drug for augmenting TGF-β activity. A test compound which decreases the amount of reporter gene transcription is a potential drug for decreasing TGF-β activity.

Another embodiment of the invention provides a recombinant construct which comprises a reporter gene under the control of an activin response element. The activin response element comprises an hFAST-1 binding motif TGT(G/T)(T/G)ATT as shown in SEQ ID NO:4.

A further embodiment of the invention provides a double-stranded DNA fragment which comprises an activin response element. The activin response element comprises an hFAST-1 binding motif TGT(G/T)(T/G)ATT as shown in SEQ ID NO:4. The fragment is covalently attached to an insoluble polymeric support.

Even another embodiment of the invention provides an isolated and purified oligonucleotide which encodes at least thirteen contiguous amino acids of hFAST-1 protein as shown in SEQ ID NO:2.

Yet another embodiment of the invention provides an isolated and purified oligonucleotide which comprises at least 19 contiguous nucleotides of hFAST-1 as shown in SEQ ID NO:1.

The invention thus provides the art with novel tools and systems with which to probe and modify the molecular events of the TGF-β signal transduction pathway which result in transcriptional activation.

BRIEF DESCRIPTION OF THE DRAWINGS

FIG. 1 displays the sequence of hFAST-1 (SEQ ID NO:2) and compares it to the Xenopus homolog (SEQ ID NO:19). Conserved amino acids are shaded. The forkhead domain encompasses xFAST-1 residues 108 to 219 (SEQ ID NO:19) (Chen et al., 1996). The C-terminal Smad-interacting domain (SID) encompasses xFAST-1 residues 380 to 506 (SEQ ID NO:19) (Chen et al., 1997).

FIGS. 2A–2B illustrate the expression of hFAST-1 and its interaction with Smad2.

FIG. 2A demonstrates that hFAST-1 was expressed in all tissues tested. RNA samples prepared from the indicated tissues were used as templates for RT-PCR analysis. The PCR primers used span a 100-bp intron and discriminate the spliced (423 bp) and unspliced (523 bp) RT-PCR products. The unspliced products arose from either genomic DNA or from unprocessed transcripts.

FIG. 2B shows that both full-length hFAST-1 (FAST-FL) and its carboxyl-terminus (FAST-SID) could interact with the carboxyl-terminal (MH2) domain of Smad2 in vitro. Polypeptides encoding full-length hFAST-1 or its SID domain were generated by in vitro translation in the presence of $^{35}$S-labeled methionine and incubated with a GST-fusion protein containing the carboxyl terminus of Smad2 (GST-Smad2/MH2) immobilized on agarose beads. An irrelevant protein (PIG3, Polyak et al., 1997) was also translated and incubated with GST-Smad2/MH2 as a control. After extensive washing, the bound proteins were eluted and separated in a 4–20% SDS-Tris-glycine gel which was dried and autoradiographed. Ten percent of the in vitro translated proteins used for binding to Smad2 were applied to the lanes labeled "Total."

FIG. 3A shows that hFAST-1 mediated transcriptional activation requires TGF-β. MvLu1 cells were transfected with pAR3-lux with or without pCMV-hFAST-1 (FAST-1). The transfected cells were cultured in the presence or absence of TGF-β1 (1 ng/ml). Twenty hours following transfection, cells were harvested and luciferase activity measured. The results were normalized to the control in which cells were neither transfected with pCMV-hFAST-1 nor treated with TGF-β. Bars and brackets represents the means and standard deviations calculated from triplicate transfections.

FIG. 3B shows that activin signaling leads to hFAST-1 mediated transcriptional activation. HCT116 cells were cotransfected with pAR3-lux, pCMV-hFAST-1 (FAST-1), and the constitutively active activin receptor ActRIB* as indicated. Luciferase activity was analyzed 20 hours later and the results normalized to controls transfected with reporter but without pCMV-hFAST-1 or ActR1B*.

FIG. 3C demonstrates that hFAST-1-mediated transcriptional activation requires Smad4 and a functional hFAST-1 forkhead domain. HCT116 cells or their Smad4-deficient derivatives (5–18) were transfected with pAR3-lux plus pCMV-hFAST-1 (wt [FAST-1] or mutant H83R [FAST-1*]) plus the RII receptor for TGF-β as indicated. All cells were treated with TGF-β1 for 20 hours prior to harvest. Luciferase activity was normalized to the control in which cells were not transfected with pCMV-hFAST-1 or RII.

FIGS. 4A–4D demonstrate the sequence-specific DNA binding of hFAST-1.

FIG. 4A shows examples of an electrophoretic mobility shift analysis (EMSA) of mock-selected or hFAST-1-selected clones. $^{32}$P-labeled PCR products generated from individual clones were incubated with a GST-fusion protein containing full length hFAST-1 sequences. Derivation of clones and EMSA were performed as described in Example 7. Mock selected clones were used for comparison ("C" lanes). The positions of free probe and hFAST-1 bound probe ("shift") are indicated.

FIG. 4B provides a sequence summary of clones that bound to hFAST-1. The sequences of the relevant segment of 17 hFAST-1-binding clones were determined and the fractions of clones containing the nucleotides at the indicated positions relative to the consensus are shown.

FIG. 4C demonstrates the binding of FBE to hFAST-1. Wild-type (FBE) or mutant (FBE*) oligonucleotides were incubated with 0.5–2.0 μg of GST fusion proteins containing full-length hFAST-1 (FAST-FL) or only its forkhead domain (FAST-FH). GST fusion proteins containing the MH1 or MH2 domains of Smad2 (S-N and S-C, respectively; Zawel et al., 1998) were used as controls. The FBE* oligonucleotide contained the sequence TCTGTATC in place of the consensus TGTGTATT but was otherwise identical to FBE.

FIG. 4D demonstrates the binding of ARE oligonucleotides to hFAST-1. EMSA was performed with (+) or without (–) 1 μg of GST fusion protein containing full length FAST-1 ("FAST-FL"). The sequence of the 50 bp ARE oligonucleotide differed by only one bp from ARE*.

DETAILED DESCRIPTION OF THE INVENTION

Figure 3A:
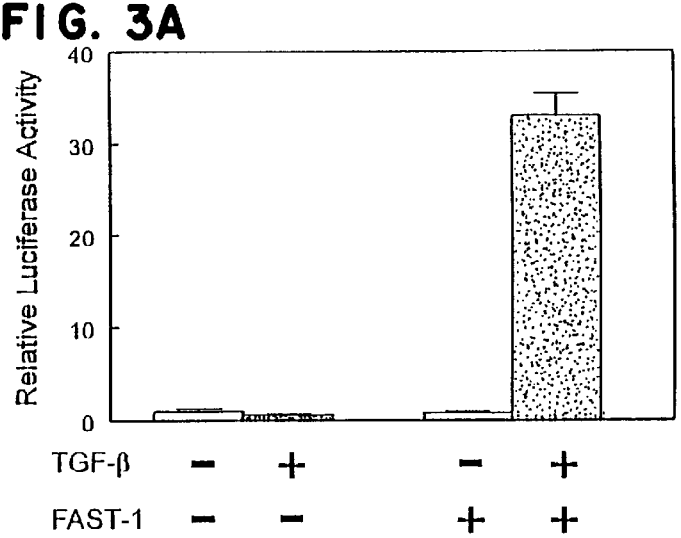
FIGS. 3A–3C demonstrate hFAST-1 mediated transcriptional activation.

We have isolated and characterized a human homolog of Xenopus FAST-1, termed hFAST-1. hFAST-1 mediates transcriptional responses to TGF-β and activin in a ligand-, receptor-, and Smad-dependent fashion.

hFAST-1 protein consists of 365 amino acid residues which are shown in SEQ ID NO:2 and FIG. 1. A nuclear localization domain is found at residues 22–30, and the adjacent downstream region (approximately residues 33–154) is presumed to contain the forkhead DNA-binding domain. The Smad2 binding domain is found near the carboxy terminus.

The invention also includes naturally occurring biologically active variants of hFAST-1. Naturally occurring biologically active variants of hFAST-1 include proteins which have, for example, conservative amino acid substitutions of amino acids of SEQ ID NO:2. Such variants can result, for example, from polymorphisms in an hFAST-1 coding sequence. Biologically active variants of hFAST-1 possess similar biological activity to that of the hFAST-1 protein shown in SEQ ID NO:2, such as the ability to bind to Smad2, to bind to the ARE binding motif of SEQ ID NO:4, and to activate transcription.

hFAST-1 polypeptides consist of at least 13, 14, 15, 17, 20, 25, 30, 35, 40, 45, 50, 60, 70, 80, 87, 88, 100, 120, 140, 144, 145, or 150 contiguous amino acids of hFAST-1 as shown in SEQ ID NO:2. Polypeptides can also comprise regions of the hFAST-1 amino acid sequence which are involved in the binding of hFAST-1 to Smad2. Such regions are located near the carboxy terminus of hFAST-1, e.g., in the region from positions 277–364 or 221–365 of SEQ ID NO:2. Polypeptides can also comprise the nuclear localization region of hFAST-1, amino acids 22–30. An hFAST-1 protein or polypeptide can be isolated by physical separation from the cells in which it is produced and separation from most of the other proteins produced by the cells. Standard purification techniques such as affinity or ion exchange chromatography, as well as any other technique known in the art, can be used to purify the protein or polypeptide. A protein or polypeptide preparation is purified when it exists as a nearly homogeneous mixture consisting of at least about 70, 75, 80, 85, 90, 95, 98, or 99% of the desired molecular species.

hFAST-1 protein or polypeptides can also be produced by recombinant DNA methods or by synthetic chemical methods. For production of recombinant hFAST-1 protein or polypeptides, for example, the coding sequence shown in SEQ ID NO:1 can be expressed in known prokaryotic or eukaryotic expression systems. Bacterial, yeast, insect, or mammalian expression systems can be used, as is known in the art. Alternatively, synthetic chemical methods, such as solid phase peptide synthesis, can be used to synthesize an hFAST-1 protein or polypeptide.

The invention also provides non-naturally occurring fusion proteins which comprise all or a portion of hFAST-1. In such a fusion protein, a first protein segment is fused to a second protein segment by means of a peptide bond. The first protein segment consists of at least 13, 14, 15, 17, 20, 25, 30, 35, 40, 45, 50, 60, 70, 80, 87, 88, 100, 120, 140, 144, 145, or 150 amino acids of hFAST-1 as shown in SEQ ID NO:2. The second protein segment can be all or a portion of any protein whose structure or function is desired to be combined with that of hFAST-1. An hFAST-1 fusion protein can be produced by using standard recombinant DNA techniques to combine the sequences of the desired first and second protein segments into an expression vector, which is introduced into a cell or cell line that is subsequently induced to express the fusion protein. The fusion protein may either be used within the cell or cell line containing the vector or it can be isolated and optionally purified from the cell or cell line, or from the culture medium, using standard cell homogenization, extraction, and protein purification methods.

Antibodies can be prepared which specifically bind to epitopes of an hFAST-1 protein, polypeptide, or fusion protein. Such antibodies can be immunoglobulins of any class, i.e., IgG, IgA, IgD, IgE, or IgM. The antibodies can be obtained by immunization of a mammal such as a mouse, rat, rabbit, goat, sheep, primate, human, or other suitable species. The antibodies can be whole immunoglobulins or fragments thereof, provided that specific binding for hFAST-1 epitopes is maintained. Antibodies to hFAST-1 can be the result of genetic engineering, e.g., interspecies or chimeric antibodies. The antibodies can be polyclonal antibodies which are obtained from the serum of an immunized animal, i.e., antiserum. The antibodies can also be monoclonal antibodies, formed by immunization of a mammal with an hFAST-1 antigen, fusion of lymph or spleen cells from the immunized mammal with a myeloma cell line, and isolation of specific hybridoma clones, as is known in the art.

hFAST-1 antibodies can, if desired, be purified by any method known in the art, e.g., affinity purification using a column with hFAST-1 antigen as the affinity ligand. The antibodies can be eluted from the column, for example, using a buffer with a high salt concentration.

Antibodies which specifically bind to hFAST-1 proteins, polypeptides, or fusion proteins provide a detection signal at least 5-, 10-, or 20-fold higher than a detection signal provided with other proteins when used in Western blots or other immunochemical assays. Preferably, antibodies which specifically bind to hFAST-1 epitopes do not detect other proteins in immunochemical assays and can immunoprecipitate a hFAST-1 protein, polypeptide, or fusion protein from solution.

The invention also provides isolated subgenomic polynucleotides which encode hFAST-1 protein and polypeptides. Subgenomic polynucleotides contain less than a whole chromosome. Preferably, the polynucleotides are intron-free. One subgenomic polynucleotide encodes the hFAST-1 protein shown in SEQ ID NO:2. hFAST-1 polynucleotide molecules can also comprise a contiguous sequence of at least 10, 11, 12, 15, 19, 20, 25, 30, 32, 35, 37, 40, 45, 50, 60, 70, 74, 80, 90, or 100 nucleotides selected from SEQ ID NO:1. Optionally, a subgenomic polynucleotide can comprise the nucleotide sequence of SEQ ID NO:1.

The complement of the nucleotide sequence shown in SEQ ID NO:1 is a contiguous nucleotide sequence which forms Watson-Crick base pairs with a contiguous nucleotide sequence shown in SEQ ID NO:1 and is also a subgenomic polynucleotide, which can be used to provide hFAST-1 antisense oligonucleotides. A double-stranded polynucleotide which comprises the nucleotide sequence shown in SEQ ID NO:1 is also a subgenomic polynucleotide.

Isolated and purified oligonucleotides which encode at least 13 contiguous amino acids of hFAST-1 protein as shown in SEQ ID NO:2, or which comprise at least 19 contiguous nucleotides of SEQ ID NO:1, are also included as subgenomic polynucleotides.

The hFAST-1 gene can be isolated by the method described in Example 1. The gene is isolated when it is obtained free from unrelated polynucleotide sequences, leaving only coding, non-coding, and regulatory sequences associated with the expression of hFAST-1 protein.

hFAST-1 subgenomic polynucleotides can be isolated and purified free from other nucleotide sequences using standard nucleic acid purification techniques. For example, restriction enzymes and probes can be used to isolate polynucleotide fragments which comprise nucleotide sequences encoding hFAST-1 protein. Isolated and purified subgenomic polynucleotides are in preparations which are free or at least 90% free of other molecules. Optionally, hFAST-1 subgenomic polynucleotides can contain sequences from non-coding regions of the hFAST-1 gene, such as introns, or sequences from a promoter region or transcription terminator region.

In order to clone, replicate, modify, express, or otherwise manipulate hFAST-1 subgenomic polynucleotides, sequences of hFAST-1 can be incorporated into a recombinant construct. A recombinant construct can be a linear or circular polynucleotide, e.g., a viral DNA or RNA or a plasmid. Optionally, a recombinant construct is capable of transferring desired nucleotide sequences into a prokaryotic or eukaryotic cell. The construct can be a vector and can contain additional nucleotide sequences such as replication origins, promoters, transcription terminators, and reporter genes to facilitate replication, insertion into the host cell genome, expression, or detection of the vector. For example, an expression vector can comprise a promoter capable of activating expression in a host cell.

Vectors or recombinant constructs can be prepared by standard recombinant DNA techniques. Vectors or other recombinant constructs containing either native or modified hFAST-1 sequences or fragments thereof can optionally contain sequences from other proteins so as to create fusion proteins or can contain reporter gene sequences. Protein sequences which serve as portions of fusion proteins or as reporter genes can be from any human or non-human protein. Any reporter gene, such as the genes for green fluorescent protein (GFP), luciferase, chloramphenicol acetyltransferase, or β-galactosidase, can be incorporated into such vectors or constructs in order to facilitate determination of the level or localization of expression of hFAST-1 proteins or polypeptides. The expression of such reporter genes can be detected, for example, as fluorescence or as enzyme activity or by standard immunocytochemical techniques.

hFAST-1 subgenomic polynucleotides can be incorporated into an expression vector which is then used to transfect an appropriate cell line, and used to produce hFAST-1 protein, polypeptides, or fusion proteins containing all or a portion of hFAST-1. Using the sequence information for hFAST-1 shown in SEQ ID NOS:1 and 2, variants of hFAST-1 can be constructed which retain all or a portion of the biological activity of hFAST-1.

A vector can be introduced into a suitable host cell by standard transfection techniques, to produce a recombinant host cell. Transfection with an hFAST-1 vector can be either transient or stable, as required by the particular needs of an hFAST-1 expression protocol.

The recombinant host cell is a cell or cell line which is suitable for transfection by the vector and for expression of the hFAST-1 protein or polypeptide. Many different cell types are suitable as the recombinant host cell. Examples of such cells are the cells of bacteria, yeast, insects, amphibians, and mammals, such as a mouse, rat, primate, human, or other suitable species. Recombinant host cells can also be tumor cells grown either in cell culture or in an animal, such as a nude mouse.

The orientation of hFAST-1 coding sequences in a recombinant construct or an expression vector relative to promoter and transcription terminator sequences can be as found in the native hFAST-1 gene or can be inverted so as to allow the production of hFAST-1 antisense oligonucleotides. If coding sequences are utilized from the sense strand of the gene, i.e., the strand which encodes the amino acid sequence of SEQ ID NO:2, expression of the encoded amino acid sequence will result. If sequences from the complementary (antisense) strand are utilized, then upon transcription from the promoter, an RNA will be produced which is complementary to native mRNA encoding hFAST-1. Antisense hFAST-1 oligonucleotides can be used to decrease expression of hFAST-1. Optionally, the recombinant construct or vector can also comprise a transcription terminator, in which case the inverted hFAST-1-derived sequence is located between the promoter and transcription terminator.

The invention also provides recombinant constructs and double-stranded DNA fragments which can be used, for example, in binding or transcriptional activating assays, using hFAST-1. A recombinant construct of the invention can comprise a reporter gene under the control of an activin response element. The activin response element comprises an hFAST-1 binding motif as shown in SEQ ID NO:4. Optionally, the recombinant construct can comprise a vector, as described above. Any reporter gene which produces a detectable product can be used. For example, the reporter gene can encode a non-human protein, such as green fluorescent protein, luciferase, chloramphenicol acetyltransferase, or β-galactosidase.

Double-stranded DNA fragments of the invention can comprise an activin response element. The activin response element includes an hFAST-1 binding motif, as shown in SEQ ID NO:4. Optionally, the double-stranded DNA fragment can be covalently attached to an insoluble polymeric support, such as a tissue culture plate, slide, or nylon membrane.

Any polynucleotide or oligonucleotide of this invention can be labeled using standard methods to facilitate detection. For example, polynucleotides or oligonucleotides can be radiolabeled with $^{32}$P or covalently linked to a fluorescent or biotinylated molecule.

The invention provides methods for screening for test compounds which decrease or augment TGF-β activity. Compounds which decrease or augment TGF-β activity can be used to modify or regulate transcriptional activation associated with the TGF-β signaling pathway. Such compounds can be applied therapeutically, for example, to alter the growth of tumor cells or to alter normal or abnormal developmental processes.

Test compounds can be selected from natural substances secreted, extracted, isolated, or purified from microbes, plants, or animals, or can be synthetic agents. The test compounds can be pharmacologic agents already known in the art or can be compounds previously unknown to have any pharmacological activity.

In one embodiment of the invention, a test compound is contacted with a first protein and a second protein. The first protein comprises all or a portion of Smad2, or a naturally occurring biologically active variant thereof, which is capable of binding to hFAST-1. The second protein comprises all or a portion of hFAST-1, or a naturally occurring biologically active variant thereof, which is capable of binding to the portion of the Smad2 protein. Contacting can occur in vitro. The first and second proteins can be produced recombinantly, isolated from human cells, or synthesized by standard chemical methods. The binding sites can be located on full-length proteins, fusion proteins, or polypeptides. If desired, the test compound can be contacted with one of the two proteins prior to contacting with the other protein. Optionally, the step of contacting can also be performed by contacting a test compound with a cell which expresses the first and second proteins. The cell can be a normal human cell, for example, a breast, colon, thymus, or muscle cell, or can be a related cell line.

Binding or dissociation of the first and second proteins in the presence of the test compound can be determined by measuring any of the following amounts: (a) the first protein which is bound to the second protein, (b) the second protein which is bound to the first protein, (c) the first protein which is not bound to the second protein, or (d) the second protein which is not bound to the first protein. The amount of a complex formed by the first and second proteins can also be determined. The first or second protein can be radiolabeled or labeled with fluorescent or enzymatic tags and can be detected, for example, by scintillation counting, fluorometric assay, monitoring the generation of a detectable product, or by measuring the apparent molecular mass of the bound or unbound proteins by gel filtration or electrophoretic mobility. Either the first or second protein can be bound to a solid support, such as a column matrix or a nylon membrane.

A test compound which decreases the amount of (a) or (b) or which increases the amount of (c) or (d) is a candidate compound for inhibiting the action of TGF-β. Preferably, the test compound decreases the amount of (a) or (b) or increases the amount of (c) or (d) by at least 30–40%, more preferably by at least 40–60%, 50–70%, 60–80%, 70–90%, 75–95%, or 80–98%.

In another embodiment, test compounds can be screened for their ability to decrease or augment TGF-β related activity. A cell is contacted with a test compound and with TGF-β. The cell comprises all or a portion of Smad2 protein, or a biologically active variant thereof, which is capable of binding to hFAST-1. The cell also comprises all or a portion of hFAST-1 protein, or a biologically active variant thereof, which is capable of binding to Smad2. The cell also comprises hSmad4 protein.

Smad2, hFAST-1, and hSmad4 proteins or polypeptides can be supplied to the cell, for example, by transfecting the cell with DNA constructs which encode these proteins or polypeptides. Alternatively, cell types which normally contain one or more of the proteins or polypeptides can be used, such as normal breast, colon, thymus, or muscle cells, or related cell lines.

The cell also comprises a vector. The vector comprises a reporter gene under the control of an ARE. The ARE comprises a DNA motif (hFAST-1 binding domain) as shown in SEQ ID NO:4. By measuring the level of transcription or expression of the reporter gene using standard methods, the effect of the test compound can be determined. A test compound which increases the amount of reporter gene transcription or expression is a potential drug for augmenting TGF-β activity, and a test compound which decreases the amount of reporter gene transcription or expression is a potential drug for decreasing TGF-β activity. Preferably, the test compound increases or decreases the amount of transcription or expression of the reporter gene by at least 30–40%, more preferably by at least 40–60%, 50–70%, 60–80%, 70–90%, 75–95%, or 80–98%.

In another embodiment of the invention, a two hybrid method can be used to evaluate the binding of all or portions of hFAST-1 with other proteins such as Smad2. A cell can be contacted with a test compound to screen for drugs which have the ability to decrease or augment TGF-β activity.

The cell comprises two fusion proteins, which can be provided to the cell by means of expression constructs. The first fusion protein comprises either a DNA binding domain or a transcriptional activating domain and all or a portion of an hFAST-1 protein or a naturally occurring biologically active variant of hFAST-1. The portion of hFAST-1 consists of a contiguous sequence of amino acids selected from the amino acid sequence shown in SEQ ID NO:2 and is capable of binding to Smad2. The portion of hFAST-1 can be selected so that it comprises neither a DNA binding domain nor a transcriptional activation domain. The second fusion protein comprises either a DNA binding domain or a transcriptional activating domain and all or a portion of Smad2 or a naturally occurring biologically active variant of Smad2. The portion of Smad2 is that portion which is capable of binding to hFAST-1. If the first fusion protein comprises a transcriptional activating domain, the second fusion protein comprises a DNA binding domain. On the other hand, if the first fusion protein comprises a DNA binding domain, the second fusion protein comprises a transcriptional activating domain.

The cell also comprises a reporter gene comprising a DNA sequence to which the DNA binding domain specifically binds. When the portion of hFAST-1 and the portion of Smad2 bind, the DNA binding domain and the transcriptional activating domain will be in close enough proximity to reconstitute a transcriptional activator capable of initiating transcription of the detectable reporter gene in the cell. The expression of the reporter gene in the presence of the test compound is then measured. A test compound which decreases expression of the reporter gene is a potential drug for increasing TGF-β activity. A test compound which decreases the expression of the reporter gene is a potential drug for decreasing TGF-β activity. Preferably, the test compound increases or decreases reporter gene expression by at least 30–40%. More preferably, the test compound increases or decreases reporter gene expression by at least 40–60%, 50–70%, 60–80%, 70–90%, 75–95%, or 80–98%.

Many DNA binding domains and transcriptional activating domains can be used in this system, including the DNA binding domains of GAL4, LexA, and the human estrogen receptor paired with the acidic transcriptional activating domains of GAL4 or the herpes virus simplex protein VP16 (See, e.g., G. J. Hannon et al., *Genes Dev.* 7, 2378, 1993; A. S. Zervos et al., *Cell* 72, 223, 1993; A. B. Votjet et al., *Cell* 74, 205, 1993; J. W. Harper et al., *Cell* 75, 805, 1993; B. Le Douarin et al., *Nucl. Acids Res.* 23, 876, 1995). A number of plasmids known in the art can be constructed to contain the coding sequences for the fusion proteins using standard laboratory techniques for manipulating DNA (see Example 1, infra). Suitable detectable reporter genes include the *E. coli* lacZ gene, whose expression can be measured colorimetrically (e.g., Fields and Song, supra), and yeast selectable genes such as HIS3 (Harper et al., Supra; Votjet et al., supra; Hannon et al., supra) or URA3 (Le Douarin et al, supra). Methods for transforming cells are also well known in the art. See, e.g., Hinnen et al., *Proc. Natl. Acad. Sci. U.S.A.* 75, 1929–1933, 1978.

The above disclosure generally describes the present invention. A more complete understanding can be obtained by reference to the following specific examples, which are provided herein for purposes of illustration only and are not intended to limit the scope of the invention.

EXAMPLE 1

Example 1 describes the isolation of the hFAST-1 gene.

Sequences corresponding to xFAST-1, but outside the forkhead domain, were used to search the National Center for Biotechnology Information (NCBI) nucleotide sequence database 'dbest' using the BLAST program 'tblastn'. An EST sequence (accession #AA218611) was identified based on its homology with the Smad interaction domain of xFAST-1. Primers were designed to extend the EST sequence using a RACE method. Briefly, nested PCR was performed using CLONTECH's Marathon-ready Human Colorectal Adenocarcinoma cDNA as the initial template and a set of EST-specific primers in combination with the AP1 or AP2 primers provided with the Marathon-ready cDNA. After two rounds of PCR amplification, the PCR products were gel-purified and sequenced using Thermo Sequenase (Amersham).

To ensure the correctness of the sequence, the sequences of multiple independent PCR products from cDNA and genomic DNA were determined. Multiple stop codons in all three reading frames were identified at both 5' and 3' ends of the PCR products and used to derive a long ORF defining hFAST-1. The first in-frame methionine in this ORF was assumed to be the initiation site for translation, and the sequences surrounding this methionine matched the Kozak consensus (Kozak, 1992).

A sequence alignment between hFAST-1 and xFAST-1 was carried out using the MACAW multiple alignment software (v2.01). The results are shown in FIG. 1. The coding sequence of the hFAST-1 gene is shown in SEQ ID NO:1. The corresponding amino acid sequence is shown in SEQ ID NO:2.

The hFAST-1 and xFAST-1 genes are considerably divergent. There are only two regions of significant similarity between xFAST-1 and hFAST-1, corresponding to the presumptive DNA-binding forkhead domain and the carboxyl terminal Smad-binding domain (FIG. 1). A prominent nuclear localization domain (hFAST-1 residues 22–30) was conserved at the amino-terminal end of the forkhead domain of both proteins.

EXAMPLE 2

Example 2 demonstrates expression of hFAST-1.

RT-PCR was performed with Platinum Taq DNA polymerase (GibcoBRL) and primers NT2–11 (5'-CTGGAAAGACTCCATTCG-3'; SEQ ID NO:5) and NT2–8 (5'-CACAGAGGCCTCTCAGAAG-3'; SEQ ID NO:6). These primers span an intron and thereby allow discrimination of mRNA-derived PCR products from those derived from genomic DNA or unprocessed RNA. The cDNA templates were prepared from total RNA of different normal tissues using SuperScript II reverse transcriptase (GibcoBRL) and random hexamers as primers (Thiagalingam et al., 1996).

The hFAST-1 gene appeared to be expressed in all normal human tissues tested, including those of breast, colon, thymus, and muscle, as well as in several cancer cell lines (FIG. 2A).

EXAMPLE 3

Example 3 demonstrates chromosomal mapping of the hFAST-1 gene.

A genomic clone containing hFAST-1 was obtained by screening a bacterial artificial chromosome (BAC) library. This clone was used in fluorescence in situ hybridization (FISH) analyses of human metaphase spreads, revealing that the hFAST-1 gene resided at chromosome 8q24.

For chromosomal mapping of the hFAST-1 gene, two independent BAC clones containing the hFAST-1 gene were labeled with biotin-16-dUTP by nick translation. Human prometaphase chromosome spreads were fixed on slides and pretreated with RNase and pepsin. Multicolor FISH was performed as described (Lengauer et al., 1997). Hybridization signals were detected with FITC Avidin-DCS (Vector), and chromosomes were counterstained with DAPI. The resulting banding pattern and hybridization signals were evaluated by epifluorescence microscopy with a Nikon Eclipse E800.

Fifty randomly selected prometaphases were evaluated for each clone, and each of them showed hybridization signals on the distal long arm of both chromatids at chromosomal region 8q24.3. The chromosomal location was confirmed by double hybridization of hFAST-1 sequences and a centromere probe specific for chromosome 8 (Dunham et al., 1992). Fine-mapping of hFAST-1 to the 8q24.3 band was confirmed by fractional length measurements (Lichter et al., 1990).

EXAMPLE 4

This example demonstrates sequence analysis of hFAST-1 in colon cancer cells.

Many studies have shown that TGF-β responsiveness is abrogated during tumorigenesis (Fynan and Reiss, 1993). To determine whether the hFAST-1 gene was commonly altered in cancers, its sequence was examined in 45 colorectal cancer cell lines passaged in vitro or as xenografts in nude mice. For this purpose, the structure and sequence of the gene were determined from PCR analyses of genomic DNA and cDNA, revealing two small introns, at codons 58/59 and 93/94, respectively. Genomic DNA was PCR-amplified with primers NT2–12 (5'-CCCCCTTCCATCCGAATG-3'; SEQ ID NO:7 ) and NT2–3 (5'-GAGCTGCTGTGTCGCAGAC-3'; SEQ ID NO:8). This amplification resulted in a 1750 bp PCR product containing the entire coding region of hFAST-1 plus its two introns. After gel purification, the PCR products were sequenced using Thermo Sequenase (Amersham). Complete sequence determination of the coding sequence plus the two introns in the 45 tumors revealed no variations from the wild-type sequence other than three polymorphisms (one silent change at codon 150, one serine to threonine substitution at codon 113, and one threonine to serine substitution at codon 125).

EXAMPLE 5

This example demonstrates interaction of hFAST-1 with Smad2.

To determine whether hFAST-1, like its Xenopus counterpart, would bind to Smad2, $^{35}$S-labeled proteins were generated through in vitro transcription and translation of an hFAST-1 cDNA clone. A plasmid (pGST-Smad2/MH2) expressing the carboxyl terminus of Smad2 (codons 183–467, comprising the MH2 domain (Riggins et al., 1997)) fused to GST was constructed as previously described (Zawel et al., 1998). Full-length hFAST-1 was PCR-amplified with primers NT2/flag-TNT1 (5'-GGATCCTAATACGACTCACTATAGG-GAGACCACCATGGA CTACAAGGACGACGATGA-CAAGGGGCCCTGCAG CGGCTCC-3'; SEQ ID NO:9) and primer NT2-3. A C-terminal fragment of hFAST-1 was amplified with primers NT2/flag-TNT2 (5'-GGATCCTAATACGACTCACTATAGG-GAGACCACCATGGACTACAAG GACGACGATGA-CAAGCCCCTTCCTGGCCCCACG AG-3'; SEQ ID NO:10) and primer NT2-3. As a control, the entire ORF of PIG3 (Polyak et al., 1997) was also PCR-amplified.

These PCR products were used as templates in an in vitro transcription and translation (TNT) reaction using TNT®T7 Coupled Reticulocyte Lysate System (Promega). The $^{35}$S-labeled TNT products were incubated with the GST-Smad2/MH2 fusion protein coupled to agarose beads for 2 hours at 40° C. in EBC buffer (50 mM Tris-HCl, pH 7.5, 100 mM NaCl, 0.5% NP-40). After five washes with EBC buffer at room temperature, the agarose beads were collected by brief centrifugation and the bound proteins eluted by boiling in SDS-sample buffer. The eluted proteins were separated in a 4–20% Tris-glycine gel and autoradiography was performed.

The labeled proteins were incubated with agarose beads linked to the carboxyl-terminal MH2 domain of human Smad2, previously shown to bind xFAST-1 (Chen et al., 1997; Liu, 1997). Both full length hFAST-1 and a C-terminal fragment of hFAST-1 containing residues 221 to 365 bound efficiently and specifically to the MH2 domain of Smad2, demonstrating that Smad2-binding is a conserved property of FAST-1 proteins (FIG. 2B).

EXAMPLE 6

This example demonstrates hFAST-1 mediated transcriptional activation.

In order to determine whether hFAST-1 could function in vivo as a signal transducer for TGF-β, an expression vector was constructed in which hFAST-1 was under the control of the CMV promoter (pCMV-hFAST-1). To construct the vector, normal human colon cDNA was used as the template to PCR-amplify the hFAST-1 ORF with primers NT2-exp5' (5'-TATGCGGCCGCCACCATGGGGCCCTGCAGCG-3'; SEQ ID NO:11) and NT2-exp3' (5'-TATGCGGCCGCGAGCTGCTGTGTCGCAGAC-3'; SEQ ID NO:12). The PCR product was cloned into the Not1 site of pCI-neo (Promega) and the recombinant plasmid (pCMV-hFAST-1) sequenced to ensure its integrity. Transfection was carried out as described (Zhou et al., 1998).

pCMV-hFAST-1 was transfected into the mink lung epithelial cell line MvLu1 together with the AR3-lux reporter containing three copies of the activin response element (ARE) from the Xenopus Mix.2 promoter (Chen et al., 1996; Hayashi et al., 1997). The plasmid pAR3-lux was provided by J. Wrana (The Hospital for Sick Children, Toronto). AR3-lux was activated over 30-fold by hFAST-1, and this response was completely dependent on TGF-β exposure (FIG. 3A). A similar TGF-β-dependent activity of hFAST-1 was observed in human HaCaT cells, another TGF-β responsive line.

Figure 3B:
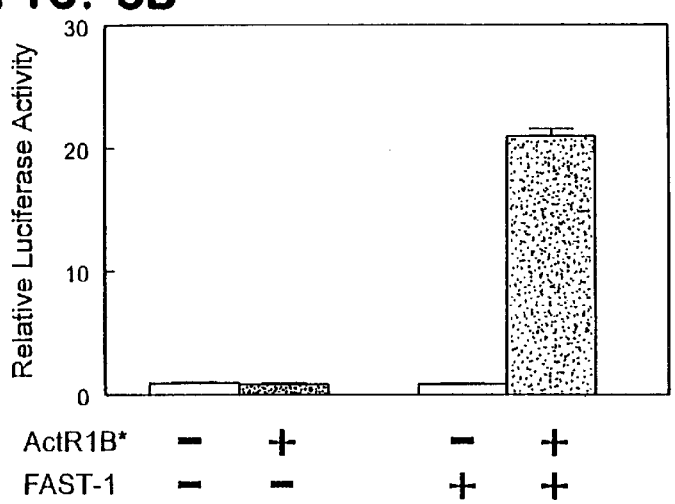

In contrast to the AR3-lux reporter, cotransfection of the hFAST-1 expression vector had no effect on the activation of the TGF-β responsive reporters p3TP-lux or SBE4-lux. Expression of an activin receptor whose kinase was engineered to be constitutively active even in the absence of ligand (Attisano et al., 1996), also conferred high levels of AR3-lux activity in the presence of co-transfected hFAST-1 (FIG. 3B).

Figure 3C:
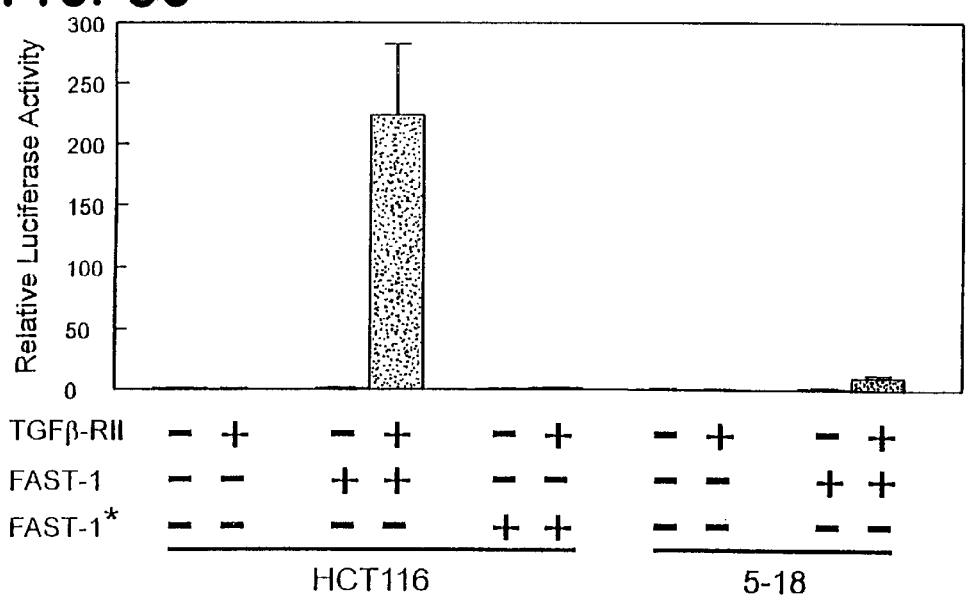

Human HCT116 cells were employed to examine other requirements for FAST-1-dependent activation of AR3-lux. The endogenous TGF-β receptor type II (RII) gene is mutated in these cells (Markowitz et al., 1995; Parsons et al., 1995), but TGF-β responses can be restored by exogenous expression of the RII gene (Wang et al., 1995; Zhou et al., 1998). The TGF-β RII expression vector has been described by Zhou et al. (1998). FIG. 3C shows that co-expression of the RII receptor was required for the TGF-β- and hFAST-1-dependent activation of AR3-lux.

To demonstrate that the activation of AR3-lux was dependent on the DNA-binding forkhead domain of hFAST-1, an hFAST-1 expression vector was generated in which a single residue within the forkhead domain was altered (arginine substituted for histidine at residue 83). Crystallographic studies of the HNF-3γ forkhead domain had shown that this histidine contacted DNA and would be expected to be critical for its activity (Clark et al., 1993). The results in FIG. 3C show that this arginine substitution totally abrogated hFAST-1 activity.

Finally, the hypothesis was tested that Smad4 is required for the hFAST-1 activation of AR3-lux. The 5–18 cell line is a derivative of HCT116 cells in which both alleles of Smad4 were disrupted by targeted homologous recombination (Zhou et al., 1998). Transfection of hFAST-1 into these cells resulted in little AR3-lux activity compared to the parental line (FIG. 3C). Thus the transcriptional activity of hFAST-1, even when overexpressed, was dependent on an intact endogenous Smad4 gene.

EXAMPLE 7

This example demonstrates sequence-specific DNA binding of hFAST-1.

Forkhead proteins are known to bind DNA in a specific fashion, with the loose consensus sequence (G/A)(T/C)(C/A)AA(C/T)A (Kaufmann and Knochel, 1996; SEQ ID NO:13). The xFAST-1 protein was discovered on the basis of its binding to the ARE within the promoter of the activin-inducible Mix.2 gene, and the responsible sequences were mapped to a six bp sequence (AAATGT) which was repeated twice within the ARE but which was not very similar to the forkhead consensus (Chen et al., 1996). To define the DNA sequences which could bind to hFAST-1, oligonucleotides were selected which could bind to the protein from a random pool. The oligonucleotides were degenerate in a 20 bp central region and were flanked on each side by 20 bp regions of known sequence. The hFAST-1-DNA complexes were separated by EMSA and the recovered DNA amplified by PCR. Following three rounds of selection and amplification, recovered oligonucleotides were cloned and individually tested for binding to hFAST-1 in EMSA.

To produce a GST-fusion protein (FAST-FL) containing the full length hFAST-1, the entire ORF of hFAST-1 was PCR-amplified and cloned into the BamH1 site of pGEX2TK (Pharmacia). A GST-fusion protein (FAST-FH) containing only the forkhead domain of hFAST-1 was constructed similarly. GST-fusion proteins containing the MH1 or MH2 domains of Smad2 were produced as previously described (Zawel et al., 1998). Proteins produced in bacteria from these vectors were purified with glutathione-agarose and used to select random oligonucleotides as previously described (Zawel et al., 1998). In brief, following binding to 1 $\mu$g of GST-FAST-1 proteins (or following "mock" reactions without added protein), EMSA was performed and the location of the DNA-protein complexes within the gels was approximated based on the mobility of complexes generated with an ARE-derived probe (Chen et al., 1996). Gel slices were homogenized, incubated at 65° C. for 30 min, and then passed through Spin-X columns (Costar). Recovered oligonucleotides were extracted with phenol-chloroform, precipitated with ethanol, re-amplified, and subjected to the next round of binding. Following completion of the third selection-amplification cycle, PCR products were cloned into pZERO2. 1 (Invitrogen).

Sixty bp probes corresponding to single clones were generated for EMSA by colony PCR using the following $^{32}$P-labeled primers: 5'-TAGTAAACACTCTATCAATTGG-3' (SEQ ID NO:14) and 5'-GTCCAGTATCGTTTACAGCC-3' (SEQ ID NO:15). To determine the oligonucleotide sequences contained within single clones, inserts were amplified by colony PCR using M13 forward and reverse primers and the PCR products sequenced using Thermo Sequenase and an SP6 primer. To test binding to PCR products derived from clones, 1.0–1.5 $\mu$g protein (~1 $\mu$M final concentration) and 50 ng of DNA (end-labeled to 2×10$^6$ dpm/$\mu$g) were used. To test binding to chemically synthesized oligonucleotides (rather than those generated through PCR), complementary oligonucleotides were synthesized and labeled with $\gamma^{32}$P-ATP and T4 polynucleotide kinase prior to annealing. The sequence of the FBE oligonucleotide was 5'-CGGATTGTGTATTGGCTGTAC-3' (SEQ ID NO:16), and the sequence of the control oligonucleotides (FBE*), containing two alterations of the FBE consensus, was 5'-CGGATTCTGTATCGGCTGTAC-3' (SEQ ID NO:17). The sequence of the ARE oligonucleotide was 5'-TATCTGCTGCCCTAAAATGTGTATTCCA TGGAAATGTCTGCCCTTCTCTCCGTAC-3' (SEQ ID NO:18). For binding to oligonucleotides, 0.3–0.5 $\mu$g of protein (~0.4 $\mu$M final concentration) and 0.5 ng of DNA (end-labeled to 2×10$^8$ dpm/$\mu$g) was used.

The inserts from 22 of 23 recovered clones bound to hFAST-1 (FIG. 4A). Comparison of the sequences of clones exhibiting hFAST-1 binding revealed a striking consensus (FIG. 4B). All clones contained two invariant three base elements separated by two G or T residues. The inferred consensus was TGT(G/T)(G/T)ATT (FIG. 4B; SEQ ID NO:4). To test whether this 8 bp consensus could indeed mediate hFAST-1 binding, an oligonucleotide containing a single copy of it was synthesized and tested in EMSA. This oligonucleotide (FBE, for FAST-1 binding element) bound efficiently to purified full length hFAST-1 protein and also (though less well) to the forkhead domain of hFAST-1 (FIG. 4C). FBE did not bind to similarly purified Smad2 proteins (FIG. 4C). An oligonucleotide in which two of the consensus positions were altered exhibited no binding to hFAST-1, documenting the specificity of the interaction (FIG. 4C).

The 8 bp consensus TGT(G/T)(G/T)ATT (SEQ ID NO:4) defined here was not related to the consensus ((G/A)(T/C) (C/A)AA(C/T)A; SEQ ID NO:13) inferred from the study of other forkhead proteins (Kaufmann and Knochel, 1996). Interestingly, the ARE element from the Mix.2 promoter contains a perfect match (TGTGTATT) to the consensus defined here. This 8 bp sequence overlapped one of the two repeats (AAATGT) which Chen et al. (Chen et al., 1996) suggested might be responsible for xFAST-1 binding, but it is likely that the TGTGTATT sequence was actually responsible for this binding. Chen et al. performed an informative experiment with a variant of the ARE which did not bind xFAST-1 complexes. Importantly, one of the three altered residues in this non-binding variant coincidentally affected the second base of the 8 bp consensus noted above, changing it to TCTGTATT (changed residue underlined). To specifically test whether the FBE was the critical element of the ARE for binding to FAST-1, we synthesized two 50 bp oligonucleotides, one comprising the entire sequence of the ARE ((Chen et al., 1996; SEQ ID NO:10) and one comprising the identical sequence except for a single base substitution within the FBE (TCTGTATT instead of TGTGTATT). Only the wild type ARE sequence bound to FAST-1 (FIG. 4D).

REFERENCES

Attisano, L., Wrana, J. L., Montalvo, E., and Massague, J. (1996). Mol. Cell. Biol. 16, 1066–1073.

Brent, R., and Finley Jr., R. L. (1997). Annu. Rev. Genet. 31, 663–704.

Chen, X., Rubock, M. J., and Whitman, M. (1996). Nature 383, 691–696.

Chen, X., Weisberg, E., Fridmacher, V., Watanabe, M., Naco, G., and Whitman, M. (1997). Nature 389, 85–89.

Clark, K. L., Halay, E. D., Lai, E., and Burley, S. K. (1993). Nature 364, 412–420.

Derynck, R., and Feng, X. H. (1997). Biochim. Biophys. Acta. 1333, F105–150.

Dunham, I., Lengauer, C., Cremer, T., and Featherstone, T. (1992). Hum. Genet. 88, 457–462.

Fynan, T. M., and Reiss, M. (1993). Crit. Rev. Oncog. 4, 493–540.

Hartsough, M. T., and Mulder, K. M. (1997). Pharmcol. Ther. 75, 21–41.

Hayashi, H., Abdollah, S., Qiu, Y., Cai, J., Xu, Y. Y., Grinnell, B. W., Richardson, M. A., Topper, J. N., Gimbrone, M. A., Jr., Wrana, J. L., and Falb, D. (1997). Cell 89, 1165–1173.

Heldin, C. H., Miyazono, K., and ten Dijke, P. (1997). Nature 390, 465–471.

Hoodless, P. A., and Wrana, J. L. (1998). Curr. Top. Microbiol. Immunol. 228, 235–272.

Kaufmann, E., and Knochel, W. (1996). Mech. Dev. 57, 3–20.

Kim, J., Johnson, K., Chen, H. J., Carroll, S., and Laughon, A. (1997). Nature 388, 304–308.

Kozak, M. (1992). Annu. Rev. Cell Biol. 8, 197–225.

Kretzschmar, M., Liu, F., Hata, A., Doody, J., and Massague, J. (1997). Genes Dev. 11, 984–995.

Kretzschmar, M., and Massague, J. (1998). Opin. Genet. Dev. 8, 103–111.

Lagna, G., Hata, A., Hemmati-Brivanlou, A., and Massague, J. (1996). Nature 383, 832–836.

Lengauer, C., Kinzler, K. W., and Vogelstein, B. (1997). Nature 386, 623–627.

Lichter, P., Tang, C. J., Call, K., Hermanson, G., Evans, G. A., Housman, D., and Ward, D. C. (1990). Science 247, 64–69.

Liu, F., Pouponnot, C., and Massague, J. (1997). Genes and Development 11, 3157–3167.

Liu, F., Hata A, J C, B., J, D., J, C., R M, H., and J, M. (1996). Nature 381, 620–623.

Liu, F., Pouponnot, C., and Massague, J. (1997). Genes Dev. 11, 3157–3167.

Macias-Silva, M., Abdollah, S., Hoodless, P. A., Pirone, R., Attisano, L., and Wrana, J. L. (1996). Cell 87, 1215–1224.

Markowitz, S., Wang, J., Myeroff, L., Parsons, R., Sun, L., Lutterbaugh, J., Fan, R. S., Zborowska, E., Kinzler, K. W., Vogelstein, B., Brattain, M., and Willson, J. K. V. (1995). Science 268, 1336–1338.

Nakao, A., Imamura, T., Souchelnytskyi, S., Kawabata, M., Ishisaki, A., Oeda, E., Tamaki, K., Hanai, J., Heldin, C. H., Miyazono, K., and ten Dijke, P. (1997). EMBO J. 16, 5353–5362.

Nakao, A., Roijer, E., Imamura, T., Souchelnytskyi, S., Stenman, G., Heldin, C. H., and ten Dijke, P. (1997). J. Biol. Chem. 272, 2896–2900.

Parsons, R., Myeroff, L. L., Liu, B., Willson, J. K., Markowitz, S. D., Kinzler, K. W., and Vogelstein, B. (1995). Cancer Res. 55, 5548–5550.

Polyak, K., Xia, Y., Zweier, J. L., Kinzler, K. W., and Vogelstein, B. (1997). Nature 389, 300–304.

Riggins, G. J., Kinzler, K. W., Vogelstein, B., and Thiagalingam, S. (1997). Cancer Res. 57, 2578–2580.

Savage, C., Das, P., Finelli, A. L., Townsend, S. R., Sun, C. Y., Baird, S. E., and Padgett, R. W. (1996). Proc. Natl. Acad. Sci. USA 93, 790–794.

Sekelsky, J. J., Newfeld, S. J., Raftery, L. A., Chartoff, E. H., and Gelbart, W. M. (1995). Genetics 139, 1347–1358.

Souchelnytskyi, S., Tamaki, K., Engstrom, U., Wernstedt, C., ten Dijke, P., and Heldin, C. H. (1997). J. Biol. Chem. 272, 28107–28115.

Thiagalingam, S., Lisitsyn, N. A., Hamaguchi, M., Wigler, M. H., Willson, J. K., Markowitz, S. D., Leach, F. S., Kinzler, K. W., and Vogelstein, B. (1996). Cancer Res. 56, 2936–2939.

Vize, P. D. (1996). Dev. Biol. 177, 226–231.

Wang, J., Sun, L., Myeroff, L., Wang, X., Gentry, L. E., Yang, J., Liang, J., Zborowska, E., Markowitz, S., Willson, J. K., and et al. (1995). J. Biol. Chem. 270, 22044–22049.

Zawel, L., Dai, J. L., Buckhaults, P., Zhou, S., Kiinzler, K. W., Vogelstein, B., and and Kern, S. E. (1998). Molecular Cell 1, 611–617.

Zhou, S., Buckhaults, P., Zawel, L., Bunz, F., Riggins, G., Dai, J. L., Kern, S. E., Kinzler, K. W., and Vogelstein, B. (1998). Proceedings of the National Academy, U.S.A. 95, 2412–2416.

---

We claim:

1. A subgenomic polynucleotide which encodes the hFAST-1 protein as shown in SEQ ID NO:2.

2. The subgenomic polynucleotide of claim 1 which is intron-free.

3. The subgenomic polynucleotide of claim 1 which comprises the sequence shown in SEQ ID NO:1.

4. A recombinant vector comprising the polynucleotide of claim 1.

5. A recombinant vector comprising the polynucleotide of claim 2.

6. A recombinant vector comprising the polynucleotide of claim 3.

7. A recombinant host cell which comprises the polynucleotide of claim 1.

8. A recombinant host cell which comprises the polynucleotide of claim 2.

9. A recombinant host cell which comprises the polynucleotide of claim 3.

10. The subgenomic polynucleotide of claim 1 which is isolated.

11. The subgenomic polynucleotide of claim 2 which is isolated.

12. The subgenomic polynucleotide of claim 1 which is isolated.

* * * * *

UNITED STATES PATENT AND TRADEMARK OFFICE
CERTIFICATE OF CORRECTION

PATENT NO. : 6,110,738
DATED : August 29, 2000
INVENTOR(S) : Shibin Zhou, *et al.*

It is certified that error appears in the above-identified patent and that said Letters Patent is hereby corrected as shown below:

Claim 12, column 32,
Line 19, "claim 1" has been deleted and in its place -- claim 3 -- has been inserted.

Signed and Sealed this

Second Day of October, 2001

*Attest:*

NICHOLAS P. GODICI
*Attesting Officer*     Acting Director of the United States Patent and Trademark Office